(12) United States Patent
Mullin et al.

(10) Patent No.: US 6,872,517 B2
(45) Date of Patent: Mar. 29, 2005

(54) EARLY DIAGNOSIS OF CANCEROUS AND PRECANCEROUS CONDITIONS BY LEAKAGE OF SIGNATURE PEPTIDES AND CARBOHYDRATES INTO THE BLOODSTREAM

(75) Inventors: James M. Mullin, Havertown, PA (US); James Thornton, Villanova, PA (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 68 days.

(21) Appl. No.: 09/853,427

(22) Filed: May 10, 2001

(65) Prior Publication Data

US 2001/0053534 A1 Dec. 20, 2001

Related U.S. Application Data

(60) Provisional application No. 60/203,271, filed on May 10, 2000, now abandoned.

(51) Int. Cl.$^7$ .......................... C12P 15/00; C12Q 1/00; C12Q 1/62; C12Q 1/58; G01N 33/53
(52) U.S. Cl. ........................ 435/4; 435/7.1; 435/7.23; 435/10; 435/12; 435/127
(58) Field of Search .......................... 435/4, 7.1, 7.23, 435/10, 12, 127

(56) References Cited

U.S. PATENT DOCUMENTS

| | | |
|---|---|---|
| 5,605,840 A | 2/1997 | Meddings et al. |
| 5,620,899 A | 4/1997 | Meddings et al. |
| 6,251,681 B1 | 6/2001 | Davies et al. |
| 6,407,058 B1 | 6/2002 | Staddon et al. |

OTHER PUBLICATIONS

Tockman et al (Cancer Res., 1992, 52:2711s–2718s).*
Achkar et al (Am. J. Gastroenterology, 1988, 83/3 (291–294).*
Freshney (Culture of Animal Cells, A Manual of Basic Technique, Alan R. Liss, Inc., 1983, NY, p. 4).*
Dermer (Bio/Technology, 1992, 12:320).*
Drexler et al (Leukemia and Lymphoma, 1993, 9:1–25).*
Zellner et al (Clin. Can. Res., 1998, 4:1797–1802).*
Hsu (in Tissue Culture Methods and Applications, Kruse and Patterson, Eds., 1973, Academic Pres, NY, see abstract, p. 764).*
Meddings JB et al, "Sucrose: A Novel Permeability Marker for Gastroduodenal Disease", *Gastroenterology* 1993:104:1619–1626.
Sutherland LR et al, "A simple, non–invasive marker of gastric damage: sucrose permeability", *The Lancet* 1994;343:998–1000.
Mullin JM et al, "Different Size Limitations for Increased Transepithelial Paracellular Solute Flux Across Phorbol Ester and Tumor Necrosis Factor–Treated Epithelial Cell Sheets",*J of Cellular Physiology* 1997;171:226–233.
Mullin JM et al, "Potential Interplay Between luminal Growth Factors and Increased Tight Junction Permeability in Epithelial Carcinogenesis", *J of Experimental Zoology* 1997;279:484–489.
Mullin JM et al, "Protein Kinase C Activation Increases Transepithelial Transport of Biologically Active Insulin", *Cancer Research* 1998;58:1641–1645.
Mullin JM et al, "Electrophysiological Differences in Normal Colon Mucosa from Diverticular Disease vs Cancer", *Digestive Diseases and Sciences* 2000;45(12):2374–2375.
Soler AP et al, "Increased tight junctional permeability is associated with the development of colon cancer", *Carcinogenesis* 1999;20(8):1425–1431.
Clarke H et al, "Modification of tight junction function by protein kinase C isoforms", *Advanced Drug Delivery Reviews* 2000;41:283–301.
Kawabata H et al, "Sucrose permeability as a means of detecting diseases of the upper digestive tract", *J Gastroenterol Hepatol* 1998;13(10):1002–6.
Meddings JB et al, "Sucrose Permeability: A Novel Means of Detecting Gastroduodenal Damage Noninvasively",*Am j Ther* 1995;2(11):843–849.
Wilairatana P et al, "Increased gastrointestinal permeability in patients with *Plasmodium falciparum* malaria", *Clin Infect Dis* 1997;24(3):430–5.
Martinez–Palomo A, "Ultrastructural modification of intercellular junctions between tumor cells", *In Vitro* 1970;6(1):15–20.
Davies RJ et al, "Epithelial impedance analysis in experimentally induced colon cancer", *Biophys J* 1987;52(5):783–90.
Davies RJ et al, "Sodium transport in a mouse model of colonic carcinogenesis", *Cancer Res* 1987;47(7):4646–4650.
Davies RJ et al, "Colonic epithelial impedance analysis in a murine model of large–bowel cancer", *Arch Surg* 1986;121:1253–1258.
Davies RJ et al, "Transmural electrical potential difference as an early marker in colon cancer", *Arch Surg* 1986;121:345–350.
Davies RJ et al, "Detection of the Cancer–Prone Colon, Using Transepithelial Impedance Analysis", *Arch Surg* 1989;124:480–484.

* cited by examiner

*Primary Examiner*—Susan Ungar
(74) *Attorney, Agent, or Firm*—Dann, Dorfman, Herrell and Skillman

(57) ABSTRACT

The present invention involves the early diagnosis of cancerous or precancerous conditions in the gastrointestinal tract by detection of a backleak of signature proteins or carbohydrates in a biological sample obtained from the gastrointestinal tract.

3 Claims, No Drawings

EARLY DIAGNOSIS OF CANCEROUS AND PRECANCEROUS CONDITIONS BY LEAKAGE OF SIGNATURE PEPTIDES AND CARBOHYDRATES INTO THE BLOODSTREAM

CROSS REFERENCE TO RELATED APPLICATIONS

This application claims benefit of U.S. provisional Patent Application No. 60/203,271, filed May 10, 2000, now abandoned.

FIELD OF THE INVENTION

The present invention generally relates to the fields of oncology, biochemistry, and immunology and to methods of early diagnosis of precancerous or cancerous conditions in a mammal and, more particularly, to a method of diagnosing precancerous or cancerous conditions in a mammal, wherein a biological sample is obtained from a gastrointestinal site of said mammal to detect the presence of a backleak of signature proteins or carbohydrates indicating tight junctional leakiness at an early stage of a cancerous or precancerous condition.

BACKGROUND OF THE INVENTION

Research has indicated that the tight junctional seal surrounding each epithelial cell in an epithelial tissue is compromised in the process of tumor formation. This has been shown by: 1) the ability of the tumor promoter class of secondary carcinogens to engender tight junctional leakiness through activation of protein kinase C (Mullin and O'Brien, 1986; Mullin et al., 1997); 2) the existence of leaky tight junctions between epithelia of human gastrointestinal tumors (Peralta Soler et al., 1999); and 3) the induction of tight junction leakiness in precancerous rat colon being exposed to primary carcinogens (Peralta Soler et al., 1999). The physiological implication of this leakiness is that it will compromise the barrier function of the entire epithelial tissue. This has in turn very important medical implications for the generation and progression of inflammatory and cancerous states (Mullin, 1998), particularly since proteins such as insulin have been demonstrated to cross these junctions intact (Mullin et al., 1998). Thus, precancerous and cancerous epithelial tight junctions will allow for diffusion of proteins and sugars from the lumen of the upper GI tract (esophagus and stomach) into the bloodstream. In addition however, the intrinsic compartmental physiology of epithelial tissues allows one to take advantage of a naturally occurring diagnostic indicator of leakiness in these tissues, an indicator which can provide a non-invasive early warning to cancerous and precancerous inflammatory states in epithelial tissues.

All epithelial cells in the body are polar, that is they possess distinct top and bottom surfaces. This structural polarity allows them to perform their two most basic functions: they can reabsorb substances in one direction or secrete other substances in the opposite direction. Secretion of acid into the stomach lumen or reabsorption of sugar from urine are both due to this structural polarity. This vectorial property holds true not just for acids, salts and sugars, but for proteins as well. Gastric epithelia generally secrete digestive enzymes such as trypsin into the lumen of the GI tract, not the bloodstream, whereas the hormones gastrin and secretin, are released in the opposite direction to enter the bloodstream (Mountcastle, Medical Physiology, 1974). This directionality is achieved by the structural polarity of the epithelial cells, but it is maintained by the tight junctional seals preventing back diffusion of substances across the epithelial barrier. As tight junctions become leaky in the process of development of epithelial cancer, backleak of these signature proteins will occur, causing their levels in the opposite fluid compartment to rise.

The present invention, relates to the early diagnosis of cancer by detection of a backleak of signature proteins in the gastrointestinal tract, considered as a continuum from the mouth to the rectum. Along this "tube" are various proteins and sugars which are vectorially secreted into the GI lumen and are specific not only to the GI tract but to specific sites in the GI tract. Salivary amylase (ptyalin) is a 55,000 molecular weight protein released by cells of the parotid gland into saliva, the first lumen of the GI tract (Dimagno, in Gastroenterology, 1980). It moves down the esophagus into the stomach simply with swallowing. Pepsinogens I and II (40,000 mw) are released into the lumen of the stomach from oxyntic glands. Once these proteins are exposed to the acidity of the lumen of the GI tract, they spontaneously form the smaller and catalytically active protein, pepsin (33,000 mw) (Mountcastle, Medical Physiology, 1974). This enzyme is functional in the stomach and upper intestine. In the lower intestine and colon, the trefoil factor, TFF3 or ITF, is secreted into the lumen. It is a 39 amino acid residue polypeptide which seems to be active in mucosal repair processes (Thim, 1997).

Tight junctional leakiness between gastrointestinal epithelia in the vicinity of the secretion of these proteins, or downstream of their secretion, will allow for their chronic leak into the bloodstream, raising their level in serum. Therefore, salivary amylase levels in serum have important diagnostic predictive value for esophageal and gastric precancerous conditions, specifically Barrett's Esophagus, atrophic gastritis and *H. pylorii* infection. Serum pepsin levels likewise have diagnostic value in precancerous gastric conditions, such as atrophic gastritis and *H. pylorii* infection. The secretion of TFF3 (ITF) in the lower intestine and colon makes its serum level predictive of precancerous leaks in the ileum and colon. For all three markers, elevated serum levels of these proteins can serve as low cost, noninvasive indicators whose presence can alert the physician to the need for the more expensive and involved endoscopic or colonoscopic follow-up procedures.

In addition to detecting leakage of signature proteins into the bloodstream, the present invention relates to detecting cancerous or precancerous conditions by leakage of signature carbohydrates from the epithelium into the bloodstream. Both leakage of signature proteins and leakage of signature carbohydrates serves as the basis for a noninvasive and relatively inexpensive screen for upper GI cancers and for precancerous and cancerous conditions throughout the GI tract. It would also serve to A similar approach could be utilized in a range of other epithelial tissues and cancers.

SUMMARY OF THE INVENTION

It is an object of the present invention to provide a method of diagnosing precancerous or cancerous conditions in a mammal by detecting the presence of a backleak of at least one signature protein in the gastrointestinal tract of said mammal.

It is another object of the present invention to provide a method of diagnosing precancerous or cancerous conditions in a mammal by detecting the presence of a backleak of at least one signature carbohydrate in the gastrointestinal tract of said mammal.

Another object of the present invention to provide a method of diagnosing precancerous or cancerous conditions in a mammal by detecting the presence of a backleak of at least one signature protein in the gastrointestinal tract of said mammal, wherein said signature protein is at least one of the group of trefoil factor, pepsin, and salivary amylase.

It is yet another object of the present invention to provide a method of diagnosing precancerous or cancerous conditions in a mammal by detecting the presence of a backleak of at least one signature carbohydrate in the gastrointestinal tract of said mammal, wherein said signature carbohydrate is at least one of the group of sucrose and mannitol.

DETAILED DESCRIPTION OF THE INVENTION 5 cc peripheral (venous) blood samples are drawn in EGTA-treated tubes to avoid clotting. Samples are immediately centrifuged at room temperature to separate plasma from cells. The supernatant plasma is aliquoted into 1 cc amounts and frozen immediately at −70° C. These aliquots are thawed at time of assay.

Serum amylase (total) is detected enzymatically. The assay is performed in the presence of an inhibitor, which is selective for specifically the salivary form of the enzyme, resulting in detection of the pancreatic form only. The difference between the total activity and the pancreatic activity is the salivary amylase (Huang and Tietz, 1982).

Pepsin is assayed enzymatically using Folin's phenol reagent. Since pepsinogens in plasma are converted to pepsin upon acidification to pH 2, the assay is in fact a measure of pepsin+pepsinogen. However a second aliquot of each plasma sample is incubated at pH 8 prior to assay, whereupon pepsin will be destroyed, but pepsinogen will be stable. The difference between the total activity and the pepsinogen activity will be pepsin (Herriot, 1955).

Intestinal-specific trefoil peptide (TFF3 or ITF) is assayed immunologically.

Determine if Epithelial Tight Junctional Leakiness Is a Property of Epithelial Tumors in the Upper Gastrointestinal Tract Using the same methods with which tight junctional leakiness was observed in tumor epithelia of human colon, tissue is obtained (by gastrectomy) from patients undergoing stomach surgery for adenocarcinoma. Where the tumor is large enough to permit taking a portion for research purposes, samples are taken of histologically normal mucosa from the edge of the excised tissue alongside portions of mucosa from the very edge of the tumor. Comparative permeability determinations are made electrophysiologically, by radiotracer flux and by use of electron dense dyes in electron microscopy, all techniques which have been published extensively. (Mullin et al., 1997; Peralta Soler et al., 1999; Mullin and McGinn, 1988).

In addition, the expression and phosphorylation state of the tight junctional protein, occludin, is analyzed in mucosal scrapes from histologically normal gastric mucosa and from mucosa at the edge of tumor.

Demonstration of the Leakage of Luminal Salivary Amylase and Sucrose Across the GI Barrier in Precancerous States in Humans Across a broad range of endoscopy patients, serum levels of salivary amylase are determined by using well-described enzymatic methods, arranging the results into four clinical groups: 1) grossly normal; 2) precancerous conditions (e.g. Barrett's esophagus, atrophic gastritis); 3) actual carcinomas/adenomas; and 4) ulcerations and other non cancer abnormalities (*H. pylori* positive tissue). Patients are asked prior to their endoscopy to swallow 200 ml of 0.5 g/ml sucrose. Sucrose leaking across the gastroesophageal mucosa into the bloodstream is analyzed in an overnight urine sample in collaboration with Dr. Jon Meddings of the Univ. of Calgary, Canada. In gastric and esophageal tissue biopsies from these same patients, the level of expression and the phosphorylation state of the tight junctional protein, occludin, is analyzed with a focus on testing for differences among the above four groups.

The Biomedical Importance of Tight Junction Regulation

Epithelia, have two key characteristics that seem to define all other more specific traits: 1) cell polarity, creating distinct apical and basal-lateral membrane domains; 2) structural integration into a barrier by means of the gasket-like intercellular sealing strands which are termed the "tight junction" (TJ) or zonula occludens. All other key characteristics of these cells, their binding proteins, receptors, transporters, secretory systems, etc. depend upon these two traits in order to fulfill their function. The most basic processes of nutrient absorption and salt and water balance cannot be achieved without these traits. Without polarity to achieve directionality, and a tight junctional band to maintain polarity and prevent paracellular backleak, there can be no unidirectional transcellular transport, one of, if not the key characteristic of higher life.

The present invention is predicated in part on the fact that the compromising of one or both of these traits has profound implications for not just the organism and its tissues, but even for the homeostasis of the individual epithelial cells. When one considers that the majority of lethal cancers are epithelial in origin (Fraumeni, et al., 1989), it is unusual that cancer research has not focused more on these two key properties.

Tight Junction Structure

With the discovery of the first TJ protein, ZO-1 (Stevenson et al., 1986), morphological approaches to TJ permeability based largely on freeze fracture electron microscopy studies (Pinto da Silva and Kachar, 1982), would now shift to Western immunoblot and immunofluorescence studies. Cingulin (Citi et al., 1988), ZO-2 (Jesaitis and Goodenough, 1994), 7H6 (Zhong et al., 1993), ZO-3 (Haskins et al., 1998) were all identified in the late 1980s and 1990s, as a concept began to emerge that the TJ was not only a complex of proteins, but a complex physically associated with the actin cytoskeleton of the cell (Madara et al., 1986). These proteins were, however, all found to be intracellular and, therefore, could not function as the extracellular barrier situated in the intercellular space.

The discovery of occludin (Furuse et al., 1993) marked the first of the extracellular proteins to be found. In fact, occludin was a membrane spanning TJ protein whose intracellular portion contained a binding site for ZO-1 (Furuse et al., 1994). Occludin's discovery was followed closely by the claudins (Furuse et al., 1998), which were viewed as extracellular occludin-associated proteins. A picture somewhat like the gears of a clock began to emerge.

Regulation of Tight Junctions by Tumor Promoting Phorbol Esters

There is extensive literature indicating that the class of tumor promoters (secondary carcinogens) called phorbol esters, can regulate TJ permeability and assembly. Phorbol esters have been known to increase TJ permeability since the early 1980s. (Ojakian, 1981; Mullin and O'Brien, 1986). This action of phorbol esters was then attributed to PKC activation by studies with a number of structurally distinct tumor promoting Protein Kinase C (PKC) activators such as teleocidin and diacylglycerols. (Mullin et al., 1990; Mullin and McGinn, 1988). In gastrointestinal cell sheets, phorbol esters likewise increase transepithelial permeability. (Hecht et al., 1994). PKC has been shown to mediate the effect of $Ca^{++}$ on TJ permeability (Tai et al., 1996).

Although most researchers fixate on the implication of this action of tumor promoters for indicating regulation of TJ permeability by PKC, a key point is frequently missed. This point is that a class of chemicals intricately involved in the processes of chemical carcinogenesis, are very potent mediators of increased TJ leakiness.

Aberrant Tight Junctions Associated With Tumors and Transformation

The first published report which indicates altered TJ structure in cancer was actually almost 30 years ago, and showed by using routine transmission electron microscopy that there is loss of electron dense TJ structure as a function of epithelial transformation. (Martinez-Palomo, 1970). Over a decade later, using freeze fracture electron microscopy, a decreased number of TJ strands was observed in transitional carcinoma of the urinary bladder compared with normal mucosa (Saito, 1984). Five years after this, decreased transepithelial impedance was recorded across the colons of mice treated with chemical carcinogens, suggesting increased functional permeability to $Na^+$ and $Cl^-$. (Davies et al., 1989). At this same time, inflammatory bowel disease linked with increased colon cancer risk was itself being linked with increased TJ permeability, not only in affected individuals but in first degree relatives as well. (Hollander 1988).

On a molecular basis, the TJ protein, ZO-1, has been shown to possess significant sequence homology to a septate tumor suppressor protein of *Drosophila*. A mutation of this protein leads to epithelial tumor formation in larvae. (Woods and Bryant, 1991; Willott et al., 1993). The interaction of the normal APC (adenomatous polyposis *coli*) colon cancer susceptibility gene product with the cell adhesion protein, beta catenin (Su et al., 1993), raises an interesting possibility that mutation of APC may affect cell adhesion and thereby TJ permeability.

Findings

It had been shown 20 years ago (Ojakian, 1981) that the phorbol ester, TPA, was capable of causing transepithelial leakiness to salts in a renal epithelial cell line. Once the phorbol esters were found to be activators of the signal transduction intermediate, PKC (Castagna et al., 1982; Nishizuka, 1984), this finding was then used as a springboard by many groups into the regulation of transepithelial permeability by PKC, and later into other signaling elements as well. (reviewed by Schneeberger and Lynch, 1992). Today it is not an exaggeration to say that many view phorbol esters as merely PKC activators and do not consider, or are even unaware of, their related role as tumor promoters.

One can view Ojakian's 1981 finding in light of the earlier findings which showed that: 1) phorbol esters were among the most powerful tumor promoting agents known (Diamond et al., 1980); and 2) tumor promoters function in epithelial carcinogenesis as second stage carcinogens which produce a nonheritable change in the cells being transformed. (Boutwell, 1974). The action of phorbol esters on epithelial TJs function in the process of epithelial tumorigenesis. Certainly the two key characteristics of epithelia (intrinsic polarity and ability to separate two fluid compartments in vivo) are abrogated in epithelial cancers as described below.

In the present invention, it was necessary to investigate what types of solutes these phorbol ester-treated epithelial TJs were now leaky to. The physiological and cell biological effects of the TJ leakiness would be in direct association with exactly what types of substances could now cross the epithelial barrier. In a different epithelial cell line (LLC-$PK_1$), it was shown that TPA also caused a rapid, dose dependent decrease in transepithelial electrical resistance ($R_t$), indicating increased permeability to $Na^+$ and $Cl^-$ (Mullin and O'Brien, 1986). It was also shown that the paracellular markers D-mannitol (mw 182) and polyethylene glycol (mw 4000) both crossed the TPA-treated epithelial cell sheet much more rapidly than they crossed a control cell sheet, and the electron dense dye, ruthenium red, was able to penetrate TJs of TPA-treated cell sheets, but not corresponding control cultures. (Mullin et al., 1996). In fact, chronic exposure of epithelial cell cultures to TPA (4 days or greater) resulted in polyp-like, multilayered foci, whose junctions were uniquely leaky to ruthenium red, whereas TJs of neighboring morphologically normal, one-cell-layer-thick areas were impermeable to the dye. Later studies demonstrated in fact that the TJs became leaky to molecules as large as 2 million mw (Mullin et al., 1997). Most important were the findings that within that molecular weight range, growth factors such as EGF and insulin had over 20-fold increased rates of flux, and that the material coming across the epithelial barrier retained biological activity. (Mullin and McGinn, 1987; Mullin et al., 1999).

The biological significance here is that luminal fluids of many epithelial tissues contain very high levels of certain growth factors (Barnard et al., 1995; Jorgenson et al., 1990; Nexo et al., 1992; Mroczkowski and Reich, 1993), whereas the receptors for these growth factors are normally found on the abluminal cell surface. (Bishop and Wen, 1994; Muto et al., 1991; Thompson, 1988; Scheving et al., 1989). Therefore if TJs become leaky to such growth factors, this results in epithelial growth factor receptors encountering their ligands at concentrations normally never seen in vivo, in turn resulting in altered states of differentiation and cell cycle regulation. (Mullin, 1997). In the present invention, it was necessary to increase in vivo the concentration of Epidermal Growth Factor (EGF) in rat colonic lumen. This does not produce any observed effect on normal rat colon epithelium. However rat colon which has been treated with the colon carcinogen, dimethylhydrazine, manifests a greater number and size of carcinomas when luminal EGF is increased. This is a direct consequence of the carcinogen's effect on colonic crypt epithelial TJs as described below.

On a molecular level, there are several published studies showing that the patterns and timing of translocation and downregulation of the alpha isoform of PKC correlate closely with the changes in TJ permeability, suggesting that this specific isoform may govern TJ permeability. (Mullin et al., 1997). Similar results are achieved by molecular overexpression of PKC-alpha. (Rosson et al., 1998). The TJ molecular target of activated PKC led to the conclusion, however, that PKC is further upstream in the signaling pathway regulating TJ permeability than first imagined.

In approaching the question of molecular targets of PKC which would transduce a signal to a state of increased TJ permeability, occludin was chosen to begin the studies. Unlike ZO-1, occludin is a membrane spanning protein and actually forms part of the TJ barrier. In comparison to claudins, occludin is a larger, more complex protein, and more is known of its structure and interactions. Exposure of epithelial cell sheets to TPA was observed to cause very little change in the localization of occludin as seen by immunofluorescence, whereas the intracellular TJ-associated protein, ZO-1, was being down regulated. Western immunoblots likewise showed that occludin was not being down regulated or translocated in association with TPA-induced TJ permeability increase. (Clarke et al., 2000, Appendix B). More important, however, was the finding that occludin's phosphorylation state was changing in association with increased TJ permeability. In fact, whereas it was expected to see an increase in occludin phosphorylation after PKC activation, the opposite was observed, namely a decrease in the threonine phosphorylation state of occludin. This finding led to the conclusion that at least one additional signaling element, a serine/threonine phosphatase, is between PKC and the occludin target. Site directed mutagenesis of conserved threonine residues on the carboxyl terminal end of occludin is necessary in order to better assess whether changes in threonine phosphorylation of occludin regulate TJ permeability.

Epithelial tissue studies have produced data that is of greater significance to the patient-based studies of this present invention. In a collaboration with Ned Z. Carp, M.D. (Lankenau, Dept. of Surgery) and using colectomy tissue from patients at Lankenau Hospital (F/N-R-92-691), it was shown that the TJs of surface epithelia of human colon carcinomas are uniformly leaky to electron dense dye, whereas those of histologically normal colon mucosa are uniformly impermeable (Peralta Soler et al., 1999, Appendix C). This was likewise true for dimethylhydrazine (DMH)-induced tumors in rat colon.

Interestingly, surface epithelia of hyperplastic or adenomatous human colon polyps were like normal mucosa, i.e. impermeable to the dye. More important were results which showed that TJ leakiness did in fact precede the onset of tumor formation. First it was observed that aberrant colon crypts increased in number as a function of increased number of weeks of DMH exposure, as numerous investigators have reported. In addition, however, weekly changes in barrier function of DMH-treated colon were examined, with an emphasis on assessing that function by means of electrophysiology ($R_t$) and transepithelial flux of $^{14}$C-D-mannitol. As the weeks of DMH exposure progressed there was an irregular but significant decline in $R_t$ and rise in D-mannitol flux, clearly indicating that TJ leakiness precedes tumor formation (Appendix D).

Increased barrier leakiness clearly relates to the increased number of aberrant crypts in that barrier. This suggests that the TJs of aberrant crypts are leaky. This proves to be very significant for the overall model since aberrant crypts are generally regarded to be the forerunners of adenomas and carcinomas in the colon mucosa.

In studies on biopsy tissue obtained from colonoscopy patients at Lankenau Hospital (F/N-R-96-978) (collaboration with James J. Thornton, M.D., Division of Gastroenterology, Lankenau), it was observed that the TJs between colonocytes of patients with Crohn's Disease or ulcerative colitis are significantly leakier than the TJs between colonocytes of histologically normal biopsies from patients without disease (abstract to 2000 Amer. Gastro. Assn. meeting, Gastroenterology 118(4): A803). These procedures, as well as those using the colectomy tissue described above, are very similar to the procedures required here for endoscopy and surgery tissue from patients at Lankenau.

Experimental Design

Determine if Epithelial Tight Junctional Leakiness Is a Property of Adenocarcinomas of the Human Upper Gastrointestinal Tract In close collaboration with the Departments of General Surgery and Pathology of Lankenau Hospital, this research group has been able to demonstrate that the tight junctions between epithelia of adenocarcinomas of human colon are leaky (relative to the tight junctions of epithelia from colon mucosa more than 10 cm distant from the edge of the tumor). The actual conduct of these studies begins with notification to this research group of upcoming colectomy surgeries. It is then necessary to prepare to receive specimens on the day of that patient's surgery, and notify the pathologist on call that day for frozen sections, that a colectomy for adenocarcinoma is forthcoming. An operating room nurse calls the research lab 5 minutes prior to colon removal. The on-call pathologist and a research group member meet in the frozen sections room, and the pathologist determines if tumor tissue and/or normal mucosa could be taken for research purposes. If this is possible, fresh tumor and normal tissue is transported back to the laboratory in Kreb's Ringer Bicarbonate saline at 4° C.

The tight junction permeability of this tissue is then analyzed in one of three ways: 1) electrophysiological measurement of transepithelial electrical resistance; 2) transepithelial flux of $^{14}$C-D-mannitol; and/or 3) penetration of the electron dense dye, ruthenium red, from the apical surface into the lateral intercellular space. These methods are described in Peralta Soler et al. (1999) and Mullin et al. (2000) (Appendices C and E) which also detail that tight junctions of tumor epithelia are leaky by each of the above three criteria.

Demonstration of the Leakage of Luminal Salivary Proteins Across the GI Barrier in Precancerous States in Humans It is necessary to functionally verify TJ leakiness in upper GI precancerous states and tumors in humans, and to determine if proteins normally sequestered in the lumen of the upper GI tract can cross the GI barrier at sites where a cancerous or precancerous lesion exists. This forms the basis of a noninvasive early detection system for upper GI cancer.

Patients coming in for endoscopic have 10 cc of (venous) blood drawn into tubes through an existing line. After centrifugation, the serum supernatant is frozen in 1 ml aliquots at −70° C. The salivary protein, salivary amylase (SA), is initially chosen for study. SA is a 55 kDa protein, immunologically and enzymatically distinct from the pancreatic form. This protein was chosen because it is vectorially secreted (luminally) into a fluid (saliva) which washes down into and over the areas where the TJ leakiness in precancerous lesions can allow for their crossing the gastroesophageal barrier into the bloodstream. Importantly, it is not produced in the area where the tumors will arise, and therefore its blood level cannot be due to tumorigenesis affecting sites of production (as seems to be the case for pepsinogen).

Salivary amylase can be assayed separately from its pancreatic form by virtue of a specific inhibitor of its activity (Huang and Tietz, 1982). The level of SA in the saliva of the same patients is analyzed by simply analyzing total amylase in sputum samples. SA is surprisingly stable over time in these clinical samples, a factor which aids the accuracy of the tests. Serum is analyzed undiluted. Saliva is diluted 1:1000 in PBS+1% BSA for analysis of SA.

Blood levels (and the ratio of blood level/saliva level) of SA is grouped according to whether the patient had a normal endoscopic evaluation, or cancerous/precancerous conditions were observed. For precancerous conditions there is interest in Barrett's esophagus, atrophic gastritis and *H. pylori*-infected tissue. Patients with active ulcerations of the upper GI tract and conditions of actual upper GI bleeding are not analyzed because here the GI barrier is breached in a macroscopic manner. The interest of the present invention is in the more subtle occurrence of leakiness of epithelial TJs in an otherwise intact epithelium (a condition which will not evidence bleeding).

A second marker solute is used for gastroesophageal permeability. Patients drink a solution of sucrose (100 gms in 200 ml water) the night before their endoscopy, and collect an overnight urine sample. It has previously been shown that sucrose is an excellent marker for ulceration-type leakiness in the upper GI tract. (Sutherland et al., 1994; Meddings et al., 1993). The reason is that sucrose cannot be transported across cells since it lacks a membrane transporter. Sucrose is normally completely broken down by sucrase/isomaltase on duodenal microvilli, entering enterocytes and the bloodstream as fructose and glucose. Sucrose per se normally is completely absent from the bloodstream. However a defect in the gastric barrier (e.g. ulceration) which would enable sucrose to diffuse undegraded into the bloodstream allows for its subsequent quantitative appearance in blood and then urine. Thus, use of sucrose as an indicator of macroscopic gastric damage (ulcer disease, IBD) can be taken to a more molecular level, namely the leakiness of epithelial TJ seals in precancerous conditions and actual carcinoma. Cell culture models (Mullin et al., 1997) predict that a molecule, such as sucrose, will diffuse through these altered, leaky TJs and enter the bloodstream. Due to sucrose's relatively small size (mw 342 vs. 56,000 for SA), it proves a superior probe to SA in this regard.

Endoscopic biopsies of normal and precancerous tissue from distal esophageal and gastric mucosa (corpus region) of these same patients is studied. First, biopsy tissue is mounted in simplified Ussing-type chambers, for overlay of the electron dense dye, ruthenium red, onto the apical surface. This allows for determination of TJ leakiness by observation, in electron micrographs, of the penetration of ruthenium red across the TJ and into the intercellular space, as previously described (Peralta Soler et al., 1999). In addition, use is made of Ussing-type tissue diffusion chambers specially designed for very small (<1 mm) tissue diameters (Harvard Apparatus) that have just recently become available, thereby allowing for transepithelial electrophysiological measurements and radiochemical flux analysis using biopsy samples. Therefore, measurements of $R_t$, as well as e.g. $^{14}$C-mannitol flux studies, can be made on human biopsy tissue as has been done previously with human surgical tissue (colectomy). (Peralta Soler et al., 1999; Mullin et al., 1997).

In addition to these physiological measurements of TJ permeability in normal versus precancerous tissue, the phosphorylation state of the TJ protein, occludin, is also examined. These studies derive from a recent observation using epithelial cell cultures that as TJ permeability increases, occludin is dephosphorylated at one or more threonine residues. Using techniques already in use, occludin is examined in biopsy tissue. (Clarke et al., 2000 [Appendix B]). Biopsy tissue is immediately placed in homogenization buffer on ice, sonicated, differentially centrifuged, and analyzed by Western immunoblot, probing with anti-occludin and antiphosphothreonine antibodies. This enables determination of whether or not the occludin expression and/or phosphorylation state is altered in precancerous tissue of the esophagus or stomach, as a correlate to changes in TJ permeability in the precancerous state.

References

Barnard, J. A., Beauchamp, R. D., Russell, W. E., DuBois, R. N., and Coffey, R. J. Epidermal growth factor related peptides and their relevance to gastrointestinal pathophysiology. *Gastroenterology* 108:564–580, 1995.

Bishop, W. P. and Wen, J. T. Regulation of Caco-2 cell proliferation by basolateral membrane epidermal growth factor receptors. *Am. J. Physiol. Gastrointest. Liver Physiol.* 267:G892–G900, 1994.

Boutwell, R. K. The function and mechanism of promoters of carcinogenesis. CRC *Crit. Rev. Toxicol.* 2:419–443, 1974.

Castagna, M., Takai, Y., Kaibuchi, K. Sano, K., Kikkawa, U., Nishizuka, Y. Direct activation of calcium-activated phospholipid-dependent protein kinase by tumor-promoting phorbol esters. *J. Biol. Chem.* 257:7847–7851, 1982.

Citi, S., Sabanay, H., Jakes, R., Geiger, B., and Kendrick-Jones, J. Cingulin, a new peripheral component of tight junctions. *Nature* 333:272–276, 1988.

Civan, M. M., Rubenstein, D., Mauro, T., and O'Brien, T. G. Effects of tumor promoters on sodium ion transport across frog skin. *Am. J. Physiol.* 248:C457–465, 1985.

Clarke, H., Soler, A. P., Mullin, J. M. Protein kinase C activation leads to dephosphorylation of occludin and tight junction permeability increase in LLC-PK1 epithelial cell sheets. *J Cell Sci* 113(Pt 18):3187–3196, 2000.

Clink, D. W., Bouwman, D. L., Weaver, D. W. Foregut mucosal defects: An etiology of hyperamylasemia. J Surg Res 34:576–580, 1983.

Coan, R., Allen, A., Pearson, J., Smith, J. Interference by lubricating jelly in ELISA assay for pepsin in gastric juice samples. Dig Dis Sci 39:893–895, 1994.

Davies, R. J., Joseph, R., Asbun, H., and Sedwitz, M. Detection of the cancer-prone colon, using transepithelial impedance analysis. *Arch. Surg.* 124:480–484, 1989.

Diamond, L., O'Brien, T. G., and Baird, W. M. Tumor promoters and the mechanism of tumor promotion. *Advances in CAncer Research* 32:1–63, 1980.

DiMagno, E. P. Laboratory Assessment of pancreatic impairment, in Gastroenterology, W. S. Haubrich, F. Schaffner and J. E. Berk, eds. (W. B Saunders Co., Philadelphia, 1980), pp. 2835–2836.

Dodane, V. and Kachar, B. Identification of isoforms of G proteins and PKC that colocalize with tight junctions. *J. Membr. Biol.* 149:199–209, 1996.

Ellis, B., Schneeberger, E. E., and Rabito, C. A. Cellular variability in the development of tight junctions after activation of protein kinase C. *Am. J. Physiol. Renal, Fluid Electrolyte Physiol.* 263:F293–F300, 1992.

Fraumeni, J. F., Hoover, R. N., Devesa, S. S., and Kinlen, J. L. Epidemiology of cancer. In: Cancer: Principles and Practice of Oncology. Philadelphia, J. B. Lippincott, 1989, pp. 196–209.

Furuse, M., Fujita, K., Hiiragi, T., Fujimoto, K., and Tsukita, S. Claudin-1 and -2: Novel integral membrane proteins localizing at tight junctions with no sequence similarity to occludin. *J. Cell Biol.* 141:1539–1550, 1998.

Furuse, M., Hirase, T., Itoh, M., Nagafuchi, A., Yonemura, S., and Tsukita, S. Occludin: A novel integral membrane protein localizing at tight junctions. *J. Cell Biol.* 123:1777–1788, 1993.

Furuse, M., Itoh, M., Hirase, T., Nagafuchi, A., Yonemura, S., and Tsukita, S. Direct association of occludin with ZO-1 and its possible involvement in the localization of occludin at tight junctions. *J. Cell Biol.* 127:1617–1626, 1994.

Grove, A. Amylase in lung carcinomas. An ultrastructural and immunohistochemical study of two adenocarcinomas, and a review of the literature. APMIS 102:135–144, 1994.

Gupta, A., Renfro, J. L. Effects of pH on phosphate transport by founder renal tubule primary cultures. *Am J. Physiol.* 260:R704–711, 1991.

Haskins, J., Gu, L. J., Wittchen, E. S., Hibbard, J., and Stevenson, B. R. ZO-3, a novel member of the MAGUK protein family found at the tight junction, interacts with ZO-1 and occludin. *J. Cell Biol.* 141:199–208, 1998.

Hecht, G., Robinson, B., and Koutsouris, A. Reversible disassembly of an intestinal epithelial monolayer by prolonged exposure to phorbol ester. *Am. J. Physiol. Gastrointest. Liver Physiol.* 266:G214–G221, 1994.

Herriot, R. M. Swine pepsin and pepsinogen, in Methods in Enzymology 2: 3–7, 1955.

Hodes, M. E., Sick, C. J., Karn, R. C., Ehrlich, C. E., Lehrner, L. M., Roth, L. M., Morley, D. J., Merritt, A. D. An amylase-producing serous cystadenocarcinoma of the ovary. Oncology 42:242–247, 1985.

Hollander, D. Crohn's disease—A permeability disorder of the tight junction. *Gut* 29:1621–1624, 1988.

Huang, W. Y., Tietz, N. W. Determinations of amylase isoenzymes in serum by use of a selective inhibitor. *Clin. Chem.* 28:1525–1527, 1982.

Izumi, Y., Hirose, T., Tamai, Y., Hirai, S., Nagashima, Y., Fujimoto, T., Tabuse, Y., Kemphues, K. J., and Ohno, S. An atypical PKC directly associates and colocalizes at the epithelial tight junction with ASIP, a mammalian homologue of *Caenorhabditis elegans* polarity protein PAR-3. *J. Cell Biol.* 143(1):95–106, 1998.

Jenecki, A., Jakubowiak, A., and Steinberger, A. Effects of cyclic AMP and phorbol ester on transepithelial electrical resistance of Sertoli cell monolayers in two-compartment culture. *Mol. Cell. Endocrinol.* 82:61–69, 1991.

Jesaitis, L. A. and Goodenough, D. A. Molecular characterization and tissue distribution of ZO-2, a tight junction protein homologous to ZO-1 and the *Drosophila* discs-large tumor suppressor protein. *J. Cell Biol.* 124:949–961, 1994.

Jorgensen, P. E., Rasmussen, T. N., Olsen, P. S., Raaberg, L., Poulsen, S. S., and Nexo, E. Renal uptake and excretion of epidermal growth factor from plasma in the rat. *Regul. Pept.* 28:273–281, 1990.

Junglee, D., Katrak, A., Mohiuddin, J., Blacklock H., Prentice H. G., Dandona, P. Salivary amylase and pancreatic enzymes in serum after total body irradiation. Clin Chem 32:609–610, 1986.

Kitahara, F., Kobayashi, K., Sato, T., Kojima, Y., Araki, T., Fujino, M. A., Accuracy of screening for gastric cancer using serum pepsinogen concentration. Gut 44:693–697, 1999.

Krishnamurthy, S., Dayal, Y. Pancreatic metaplasia in Barrett's esophagus. An immunohistochemical study, Am J. Surg Pathol 19:1172–1180, 1995.

Kullich, W., Pollmann, G., Czerwenka, C., Klein, G. Association between serum pepsinogen A and C levels, serum gastrin concentrations and *Helicobacter pylori* antibodies. Wien Med Wochenschr 149:157–161, 1999.

Madara, J. L., Barenberg, D., Carlson, S. Effects of cytochalasin D on occluding junctions of intestinal absorptive cells: further evidence that the cytoskeleton may influence paracellular permeability and junctional charge selectivity. *J Cell Biol* 102(6):2125–2136, 1986.

Marano, C. W., Laughlin, K. V., Russo, L. M., and Mullin, J. M. The protein kinase C inhibitor, bisindolylmaleimide, inhibits the TPA-induced but not the TNF-induced increase in LLC-PK1 transepithelial permeability. *Biochem. Biophys. Res. Commun.* 209:669–676, 1995.

Martinez-Palomo, A. Ultrastructural modifications of intercellular junctions between tumor cells. *In Vitro* 6:15–20, 1970.

Meddings, J. B., Sutherland, L. R., Byles, N. I., Wallace, J. L. Sucrose: a novel permeability marker for gastroduodenal disease. *Gastroenterology* 104(6):1619–1626, 1993.

Miki, K., Ichinose, M. Shimizu, A., Huang, S. C., Oka, H., Furihata, C., Matsushima, T., Takahashi, K. Serum pepsinogens as a screening test of extensive chronic gastritis. Gastroenterol Jpn 22:133–141, 1987.

Mountcastle, V. B. Medical Physiology (C. V. Mosby Company, St. Louis, 1974), p. 1186.

Mroczkowski, B. and Reich, M. Identification of biologically active epidermal growth factor in human fluids and secretions. *Endocrinology* 132:417–425, 1993.

Mullin, J. M. Potential Interplay between luminal growth factors and increased tight junction permeability in epithelial carcinogenesis. *J. Exp. Zool.* 279:484–489, 1997.

Mullin, J. M., Ginanni, N., and Laughlin, K. V. Protein kinase C activation increases transepithelial transport of biologically active insulin. *Cancer Res.* 58:1641–1645, 1998.

Mullin, J. M., Kampherstein, J. A., Laughlin, K. V., Clarkin, C. E. K., Miller, R. D., Szallasi, Z., Kachar, B., Soler, A. P., and Rosson, D. Overexpression of protein kinase C-? increases tight junction permeability in LLC-PK1 epithelia. *Am. J. Physiol. Cell Physiol.* 275:C544–C554, 1998.

Mullin, J. M., Kampherstein, J. A., Laughlin, K. V., Saladik, D. T., and Soler, A. P. Transepithelial paracellular leakiness induced by chronic phorbol ester exposure correlates with polyp-like foci and redistribution of protein kinase C-?. *Carcinogenesis* 18:2339–2345, 1997.

Mullin, J. M., Laughlin, K. V., Tongue, J. N., Russell, W. R., Reindl, D. V., Thorton J. J., Schulzke, J. D. Electrophysiological differences in normal colon mucosa from diverticular disease vs. cancer. *Dig Dis Sci* 45(12):2374–2375, 2000.

Mullin, J. M., Marano, C. W., Laughlin, K. V., Nuciglio, M., Stevenson, B. R., and Soler, P. Different size limitations for increased transepithelial paracellular solute flux across phorbol ester and tumor necrosis factor-treated epithelial cell sheets. *J. Cell. Physiol.* 171:226–233, 1997.

Mullin, J. M. and McGinn, M. T. The phorbol ester, TPA, increases transepithelial epidermal growth factor flux. *FEBS Letters* 221:359–364, 1987.

Mullin, J. M. and McGinn, M. T. Effects of diacylglycerols on LLC-PK1 renal epithelia: Similarity to phorbol ester tumor promoters. *J. Cell. Physiol.* 134:357–366, 1988.

Mullin, J. M., McGinn, M. T., Snock, K. V., and Imaizumi, S. The effects of teleocidin and aplysiatoxin tumor promoters on epithelial tight junctions and transepithelial permeability: Comparison to phorbol esters. *Carcinogenesis* 11:377–385, 1990.

Mullin, J. M., and O'Brien, T. G. Effects of tumor promoters on LLC-PK1 renal epithelial tight junctions and transepithelial fluxes. *Am. J. Physiol.* 251:C597–C602, 1986.

Mullin, J. M., Snock, K. V., Shurina, R. D., Noe, J., George, K., Misner, L., Imaizumi, S., and O'Brien, T. G. Effects of acute vs. chronic phorbol ester exposure on transepithelial permeability and epithelial morphology. *J. Cell. Physiol.* 152:35–47, 1992.

Mullin, J. M., Peralta Soler, A. P., Laughlin, K. V., Kampherstein, J. A., Russo, L. M., Saladik, D. T., George, K., Shurina, R. D., and O'Brien, T. G. Chronic exposure of LLC-PK1 epithelia to the phorbol ester TPA produces polyp-like foci with leaky tight junctions and altered protein kinase C-? expression and localization. *Exp. Cell Res.* 227:12–22, 1996.

Murray, N. R., Davidson, L. A., Chapkin, R. S., Gustafson, W. C., Schattenberg, D. G., and Fields, A. P. Overexpression of protein kinase C ?II induces colonic hyperproliferation and increased sensitivity to colon carcinogenesis. *J. Cell Biol.* 145(4):699–711, 1999.

Muto, S., Furuya, H., Tabei, K., and Asano, Y. Site and mechanism of action of epidermal growth factor in rabbit cortical collecting duct. *Am. J. Physiol. Renal, Fluid Electrolyte Physiol.* 260:F163–F169, 1991.

Nexo, E., Jorgensen, P. E., and Hansen, M. R. Human epidermal growth factor—On molecular forms present in urine and blood. *Regul. Pept.* 42:75–84, 1992.

Nishizuka, Y. The role of protein kinase C in cell surface signal transduction and tumor promotion. *Nature* 308:693–698, 1984.

Ojakian, G. K. Tumor promoter-induced changes in the permeability of epithelial cell tight junctions. *Cell* 23:95–103, 1981.

Peralta Soler, A., Miller, R. D., Laughlin, K. V., Carp, N. Z., Klurfeld, D. M. and Mullin, J. M. Increased tight junctional permeability is associated with the development of colon cancer. Carcinogenesis 20: 1425–1431, 1999.

Pinto da Silva, P. and Kachar, B. On tight junction structure. *Cell* 28:441–450, 1982.

Plebani, M., Pepsinogens in health and disease. Crit Rev Clin Lab Sci 30:273–328, 1993.

Rosson, D., O'Brien, T. G., Kampherstein, J. A., Szallasi, Z., Bogi, K., Blumberg, P. M., and Mullin, J. M. Protein kinase C-? activity modulates transepithelial permeability and cell junctions in the LLC-PK1 epithelial cell line. *J. Biol. Chem.* 272:14950–14953, 1997.

Saito, T. Ultrastructural changes on the junctional complexes in the human urinary bladder carcinoma by thin sectioning and freeze fracture. *J. Clin. Electron Micros.* 17:201–209, 1984.

Sheving, L. A., Shiurba, R. A., Nguyen, T. D., and Gray, G. M. Epidermal growth factor receptor of the intestinal enterocyte. Localization to laterobasal but not brush border memebrane. *J. Biol. Chem.* 264:1735–1741, 1989.

Schneeberger, E. E. and Lynch, R. D. Structure, function, and regulation of cellular tight junctions. *Am. J. Physiol. Lung Cell. Mol. Physiol.* 262:L647–L661, 1992.

Simons, R. M., Laughlin, K. V., Kampherstein, J. A., Desai, D. C., Shurina, R. D., and Mullin, J. M. Pentobarbital affects transepithelial electrophysiological parameters regulated by protein kinase C in rat distal colon. *Dig. Dis. Sci.* 43:632–640, 1998.

Soler, A. P., Miller, R. D., Laughlin, K. V., Carp, N. Z., Klurfeld, D. M., Mullin, J. M. Increased tight junctional permeability is associated with the development of colon cancer. Carcinog. 20:1425-1431, 1999.

Stevenson, B. R., Siliciano, J, D., Mooseker, M. S., and Goodenough, D. A. Identification of ZO-1: A high molecular weight polypeptide associated with the tight junction (zonula occludens) in a variety of epithelia. *J. Cell Biol.* 103:755–766, 1986.

Su, L.-K., Vogelstein, B., and Kinzler, K. W. Association of the APC tumor suppressor protein with catenins. *Science* 262:1734–1737, 1993.

Sutherland, L. R., Verhoef, M., Wallace, J. L., Van Rosendaal, G., Crutcher, R., Meddings, J. B. A simple, non-invasive marker of gastric damage: sucrose permeability. *Lancet* 343(8904):998–1000, 1994.

Tai, Y. H., Flick, J., Levine, S. A., Madara, J. L., Sharp, G. W. G., and Donowitz, M. Regulation of tight junction resistance in T84 monolayers by elevation in intracellular $Ca^{2+}$: A protein kinase C effect. *J. Member. Biol.* 149:71–79, 1996.

Thim, L. Trefoil peptides: from structure to function. Cell Molec. Life Sci. 53: 888–903, 1997.

Thompson, D. M., Proctor, J., Grant, M., and Thomas, C. Epidermal growth factor stimulates phosphatidylinositol turnover for ten hours in A431 cells without activation of protein kinase C. *Biochem. Biophys. Res. Commun.* 155:877–881, 1988.

Thompson, J. F. Specific receptors for epidermal growth factor in rat intestinal microvillus membranes. *Am. J. Physiol. Gastrointest. Liver Physiol.* 254:G429–G435, 1988.

Willott, E., Balda, M. S., Fanning, A. S., Jameson, B., Van Itallie, C., and Anderson, J. M. The tight junction protein ZO-1 is homologous to the *Drosophila* dics-large tumor suppressor protein of septate junctions. *Proc. Natl. Acad. Sci. USA* 90:7834–7838, 1993.

Woods, D. F. and Bryant, P. J. The discs-large tumor suppressor gene of *Drosophila* encodes a guanylate cyclase homolog localized at septate junctions. *Cell* 66:451–464, 1991.

Yahav, J., Oderda, G., Diver-Haber, A., Fradkin, A., Keller, N., Altare, F., Ansaldi, N., Jonas, A. Serum pepsinogen I in childhood Helicobacter pylori gastritis: its relation to mucosal peptic activity. Isr J Med Sci 32:56–59, 1996.

Yoshihara, M., Sumii, K., Haruma, K., Kiyohira, K., Hattori, N., Kitadai, Y., Komoto, K., Tanaka, S., and Kajiyama, G. Correlation of Ratio of Serum Pepsinogen I and II with Prevalence of Gastric Cancer and Adenoma in Japanese Subjects. Am J Gastroenterol 93:1090–1096, 1998.

Zakrzewska, I., Pietrynczak, M. The alterations in the activity of amylase and its salivary isoenzyme in the serum of patients with ovarian carcinoma, submitted to radiotherapy. Rocz Akad Med Bialymst 42:229–235, 1997.

Zhong, Y., Saitoh, T., Minase, T., Sawada, N., Enomoto, K., and Mori, M. Monoclonal antibody 7H6 reacts with a novel tight junction-associated protein distinct from ZO-1, cingulin and ZO-2. *J. Cell Biol.* 120:477–483, 1993.

We claim:

1. A method for noninvasive screening of a patient for the presence of Barrett's esophageal precancerous condition comprising the steps of:

a) administering an appropriate amount of sucrose to said patient, said patient not having ulcerative disease of the gastrointestinal (GI) tract nor bleeding therefrom;

b) collecting urine voided by said patient during a suitable time period after the administration of sucrose;

c) measuring levels of sucrose present in the urine collected in step b); and d) comparing the urine levels of sucrose in said patient with a control urine sample, wherein an increase in the urine levels of sucrose indicates said patient requires endoscopy to confirm the presence of Barrett's esophageal precancerous condition in said patient.

2. The method of claim 1, wherein said urine is collected over a 24 hour period.

3. The method of claim 1, further comprising the steps of:

e) obtaining a tissue sample from the esophageal mucosa of said patient;

f) examining tight junction (TJ) leakiness of said tissue sample; and g) comparing the TJ leakiness of said tissue sample from said patient with that from a control tissue sample, wherein an increase in the TJ leakiness of said tissue sample from said patient is indicative of the Barrett's esophageal condition in said patient.

* * * * *

UNITED STATES PATENT AND TRADEMARK OFFICE
CERTIFICATE OF CORRECTION

| | | |
|---|---|---|
| PATENT NO. | : 6,872,517 B2 | Page 1 of 1 |
| APPLICATION NO. | : 09/853427 | |
| DATED | : March 29, 2005 | |
| INVENTOR(S) | : James M. Mullin et al. | |

It is certified that error appears in the above-identified patent and that said Letters Patent is hereby corrected as shown below:

In the Specification

At column 1, line 12, please insert the following paragraph:

-- Government Support
This invention was made with government support under Grant No. CA048121 awarded by the National Institutes of Health. The government has certain rights in the invention. --

Signed and Sealed this
Twenty-fifth Day of August, 2015

Michelle K. Lee
*Director of the United States Patent and Trademark Office*